United States Patent
ElSohly et al.

(10) Patent No.: US 11,117,852 B2
(45) Date of Patent: Sep. 14, 2021

(54) **ISOLATION OF PURE CANNABINOIDS FROM *CANNABIS***

(71) Applicant: University of Mississippi, University, MS (US)

(72) Inventors: Mahmoud A. ElSohly, Oxford, MS (US); Waseem Gul, Oxford, MS (US); Mohamed M. Radwan, Oxford, MS (US); Amira Samir Wanas, Oxford, MS (US)

(73) Assignee: UNIVERSITY OF MISSISSIPPI, University, MS (US)

(*) Notice: Subject to any disclaimer, the term of this patent is extended or adjusted under 35 U.S.C. 154(b) by 0 days.

(21) Appl. No.: 16/603,226

(22) PCT Filed: Apr. 4, 2018

(86) PCT No.: PCT/US2018/026126
§ 371 (c)(1),
(2) Date: Oct. 5, 2019

(87) PCT Pub. No.: WO2018/187500
PCT Pub. Date: Oct. 11, 2018

(65) Prior Publication Data
US 2020/0039908 A1  Feb. 6, 2020

Related U.S. Application Data

(60) Provisional application No. 62/481,884, filed on Apr. 5, 2017.

(51) Int. Cl.
| | |
|---|---|
| *C07C 37/74* | (2006.01) |
| *C07C 37/82* | (2006.01) |
| *A01H 6/28* | (2018.01) |
| *A61K 31/05* | (2006.01) |
| *C07C 37/00* | (2006.01) |
| *C07C 37/86* | (2006.01) |
| *C07C 39/23* | (2006.01) |
| *G01N 30/02* | (2006.01) |
| *G01N 30/88* | (2006.01) |

(52) U.S. Cl.
CPC .............. *C07C 37/74* (2013.01); *A01H 6/28* (2018.05); *A61K 31/05* (2013.01); *C07C 37/004* (2013.01); *C07C 37/82* (2013.01); *C07C 37/86* (2013.01); *C07C 39/23* (2013.01); *G01N 30/02* (2013.01); *G01N 2030/884* (2013.01)

(58) Field of Classification Search
CPC ....... C07C 37/74; C07C 37/004; C07C 37/82; A01H 6/28
See application file for complete search history.

(56) References Cited

U.S. PATENT DOCUMENTS

| | | |
|---|---|---|
| 4,656,158 A | 4/1987 | Matsuo et al. |
| 6,365,416 B1 | 4/2002 | Elsohly et al. |
| 2015/0045282 A1 | 2/2015 | Elsohly et al. |

FOREIGN PATENT DOCUMENTS

| | | |
|---|---|---|
| WO | WO 98/18788 A1 | 5/1998 |
| WO | WO9818788 | 5/1998 |
| WO | WO2008134668 A2 | 11/2008 |

OTHER PUBLICATIONS

International Search Report dated Jun. 11, 2018 in PCT/US2018/026126.
Written Opinion of the International Search Authority dated Jun. 11, 2018 in PCT/US2018/026126.
EP Search Opinion for Application No. 18 781 793.7.
Mohapatra, et al., "Efficient and selective cleavage of the tert-butoxycarbonly (Boc) group under basic condition", 2005, ARKIVOC 2005:20-28.

*Primary Examiner* — Sikarl A Witherspoon
(74) *Attorney, Agent, or Firm* — Thomas | Horstemeyer, LLP (57) ABSTRACT

$\Delta^9$-Tetrahydrocannabinol ($\Delta^9$-THC or THC) and cannabidiol (CBD) are major constituents of the *Cannabis* plant that have pharmacological properties with potential therapeutic value. This invention is directed to processes for large scale isolation of these two and other cannabinoids from the *Cannabis sativa* plant. This is accomplished through the discovery that protected amino acid esters of the cannabinoids are easier to separate using normal phase silica column chromatography. Mild base hydrolysis of the esters regenerates the free cannabinoids in a purified form. The invention is also applicable to the isolation of other cannabinoids from *Cannabis* extracts.

13 Claims, 4 Drawing Sheets

ISOLATION OF PURE CANNABINOIDS FROM CANNABIS

FIELD OF THE INVENTION

The present invention relates to the isolation of pure cannabinoids from Cannabis.

BACKGROUND OF THE INVENTION

While delta-9-tetrahydrocannabinol ($\Delta^9$-THC, 1) is the main biologically active component in the Cannabis sativa plant, and because the plant and its crude drug marijuana have been used (and abused), other cannabinoids such as cannabidiol (CBD, 2) have their own activities that promise utility in the treatment of many disease conditions. THC has been approved by the Food and Drug Administration (FDA) for the control of nausea and vomiting associated with chemotherapy and for appetite stimulation of AIDS patients suffering from the wasting syndrome. The drug, however, shows other biological activities which lend themselves to possible therapeutic applications, such as in the treatment of glaucoma (1), migraine headaches (2, 3), spasticity (4), anxiety (5), and as an analgesic (4). It is because of these promising biological activities of THC that marijuana has been brought into medicinal use as a drug by many states in the USA despite the abuse potential of the drug and its illegal status on the federal level.

One of the main points brought by the medicinal marijuana proponents is the fact that the currently available soft gelatin capsule formulation is very expensive and lacks consistency in its effects. The latter point could be explained since oral THC has erratic absorption from the gastrointestinal tract, is subject to the first-pass effect resulting in heavy metabolism with production of high levels of 11-OH-THC, and undesirable side effects. Another THC formulation which was proposed for development is a pro-drug consisting of THC hemisuccinate formulated in a suppository base (6). This formulation appeared to overcome all the problems associated with the oral preparation and has been shown to produce consistent bioavailability in animal studies (7). Preliminary clinical investigations showed promise for this formulation (8, 9, 10).

Regardless of which formulation is to be used for THC or a pro-drug thereof, a source for the active pharmaceutical ingredient is critical. The currently-marketed capsule formulation contains THC prepared by an expensive synthetic process. A more economical process is needed. Our research indicates that the process describe herein in which THC is isolated from the Cannabis plant material will be less expensive at the commercial scale than the synthetic process.

$\Delta^9$–THC (1)

CBD (2)

A second major phytocannabinoid, CBD (2), has attracted much attention for development as a pharmaceutical product for the treatment of several conditions because of its reported anxiolytic, anti-psychotic, antiemetic, anti-convulsant, and anti-inflammatory properties (11-13). Most notably it has been reported that a CBD extract ("CBD") oil may be effective in the treatment of intractable epilepsy in young children (Dravet Syndrome) (14).

U.S. Pat. No. 8,071,641 B2 describes the use of CBD to suppress diabetes and protect Langerhans islets from immunogenic destruction (insulitis) in NOD mice (15).

Recently, Iannotti et al. (2014) evaluated the anticonvulsant effects of CBD and CBDV (Cannabidivarin) through TRPV1 channel activation and desensitization and in an in vitro model of epileptiform activity, and they concluded that CBD and CBDV dose-dependently activate and rapidly desensitize TRPV1, as well as TRP channels of subfamily V type 2 (TRPV2) and subfamily A type 1 (TRPA1), which could be a potential treatment for epilepsy (16).

The application of CBD for the treatment of autoimmune hepatitis was patented by Nagarkatti et al. (2012). Both natural and synthetic CBD were tested, and the inventors claimed that CBD can trigger apoptosis in immune cells and act as anti-inflammatory/immuno-suppressive agent in treating hepatitis (17).

Cannabinoid-containing plant extracts used as neuroprotective agents were studied by Guy and Platt (2014), and it was found that both CBD and THC-containing plant extract reduced the concentration of intracellular calcium ions which could be of great potential as neuroprotective agents (18).

Several investigations have been carried out over the years to isolate THC and CBD from the plant material, mostly to determine its chemical structure or to investigate the phytochemistry of the plant. The first isolation of the naturally-occurring THC in its pure form was reported by Gaoni and Mechoulam in 1964 (19). Delta-9-trans-tetrahydrocannabinol was isolated from the hexane extract of hashish by repeated column chromatography on florisil and alumina. Further purification was carried out by the preparation of the crystalline 3,5-dinitrophenylurethane of THC followed by mild basic hydrolysis to get the pure THC. The purity of THC was proven by thin layer chromatography (TLC) and spectroscopic analysis (IR and NMR).

ElSohly and Ross reported a large-scale isolation and purification process for THC from the Cannabis plant material that involved extraction with a non-polar solvent, vacuum distillation of the extract and repeated chromatography of the distillate (20). Purification of the THC in the distillate reported by ElSohly and Ross was further investigated by J. R. Duchek (21). A crystalline aryl sulfonyl derivative was prepared which upon repeated crystallization produced ≥98% pure THC after base hydrolysis. Although the ElSohly and Ross method accomplished significant purification of THC from *Cannabis*, it involved chromatographic steps that required reversed phase silica High Performance Liquid Chromatography (HPLC) to provide significant purification and, in the meantime, low concentrations of other cannabinoids were found in the final product that would have made it difficult to meet the stringent regulatory requirements for active pharmaceutical ingredients. On the other hand, while the purification of THC by repeated crystallization of the tosylate ester (21) produced a pharmaceutical grade of THC, the yield was very low (approximately 25% recovery of the THC in the original extract).

Therefore, a method is needed that could result in the isolation of THC from *Cannabis* that involves the use of normal phase chromatography and a final product of >98% purity that meets the GMP requirements. THC produced by such a method from a natural source would offer an alternative to synthetic THC, which is not easily accessible, and will encourage the development of other (non-oral) formulations with better pharmacokinetic profiles that can bypass the first pass effect encountered by oral administration of THC and avoid the side effects associated with the oral product.

Cannabidiol (CBD, 2) was isolated for the first time from the purified red oil of Minnesota wild hemp in 1940 as a pale yellow resin. Its purification was achieved through the preparation of a crystalline di-ester bis-3,5-dinitrobenzoate of CBD, then ammonolysis of it gives CBD (22). CBD was crystallized from petroleum ether as white rods (23). Preparative isolation of CBD from a *Cannabis* hexane extract was achieved by Centrifugal Partition Chromatography (CPC) using hexane/acetone/acetonitrile as solvent, but the purity of the obtained CBD was 92.7% (24).

Recently, pure CBD was isolated from the acetone extract of a fiber type *Cannabis* using silica gel column chromatography eluted with petroleum ether/ether gradient (25).

In 2006, Flockhart et al. patented the isolation of CBD from a high CBD variety of *Cannabis* (chemovars) which has a CBD content >90% of the total cannabinoids. The dried plant material was decarboxylated by heating at 105° C. for 15 minutes, then heating at 145° C. for 55 minutes. The plant material was then extracted by liquid carbon dioxide for 10 hours followed by winterization using ethanol to get rid of unwanted materials by filtration. The ethanolic solution was cleaned by passing over charcoal, and after removal of the ethanol, CBD was crystallized from pentane. The yield of CBD starting from the ethanolic extract is about 33% (26).

Synthetic CBD is commercially available but expensive. Furthermore, HPLC analysis showed the presence of ~1% THC (26).

Most of the methods used to isolate THC and CBD were based on small amounts and not for large scale. If THC and CBD are to be prepared on large scale (kilogram) quantities, an efficient and economic method is needed.

The inventors have therefore focused on the purification of THC and CBD from extracts of *Cannabis* and have developed an efficient and inexpensive method for the large-scale production of pure THC and pure crystalline CBD from different varieties of *Cannabis*.

Furthermore, the process lends itself to the isolation of other cannabinoids with potential therapeutic value such as $\Delta^9$-tetrahydrocannabivarin (THCV), cannabigerol (CBG), Cannabinol (CBN), cannabidivarin (CBDV), as well as other cannabinoids.

SUMMARY OF THE INVENTION

The present invention provides scalable, efficient and economic processes to produce THC and CBD from different varieties of *Cannabis sativa*. It has been discovered that the chromatographic separation of the different natural cannabinoids on normal-phase silica (which is extremely difficult) is much improved if one prepares the t-boc-protected amino acid esters before chromatography. This process is high yield, easily scalable and very economic. Furthermore, the isolated esters are stable and can be stored for a long time until needed, and only then they can easily be hydrolyzed under mild basic conditions to generate the desired free cannabinoid, without loss.

The approach to be followed in this method will be to acquire *Cannabis* extracts of relatively high concentration of the desired cannabinoid (for example, high THC content to produce THC, and high CBD content for CBD production), either through procurement or through extraction of the appropriate *Cannabis* variety biomass. The crude extract could be used as is in the process or could be distilled by thin film distillation prior to derivatization. The distillate or the crude extracts are then derivatized to prepare the t-boc-protected amino acid esters of the cannabinoids in the extract. Different amino acid (AA) derivatives were prepared and evaluated using TLC to select the AA derivative that results in the best separation of the desired cannabinoid. Therefore, in principle, the process is universal for all cannabinoids by changing the amino acid derivative based on the composition of the extract and the specific cannabinoid to be isolated. The derivatized extract is then subjected to normal phase chromatography to separate the pure cannabinoid derivative.

The purified derivative(s) is/are then subjected to mild basic hydrolysis to generate the free cannabinoid, the purity of which is established by GC/FID, GC/MS, and HPLC.

ABBREVIATIONS

CBD: Cannabidiol
$\Delta^9$-THC and THC: $\Delta^9$-Tetrahydrocannabinol
CBG: Cannabigerol
THCV: $\Delta^9$-Tetrahydrocannabivarin
CBN: Cannabinol
GC/FID: Gas Chromatography with Flame Ionization Detector
GC/MS: Gas Chromatography with Mass Spectrometry
DCM: Dichloromethane
Si: Silica Gel
DCC: N,N'-Dicylcohexylcarbodiimide
TLC: Thin Layer Chromatography
DMAP: 4-(dimethylamino)pyridine
Boc-Trp-OH: Nα-(tert-Butoxycarbonyl)-L-tryptophan
Boc-Gln-OH: Nα-(tert-Butoxycarbonyl)-L-glutamine
EtOAc: Ethyl Acetate
HCl: Hydrochloric acid
KOH: Potassium hydroxide
TMS: Trimethylsilyl
HPLC: High Performance Liquid Chromatography
Adduct: Chemical Addition Product
MeOH: Methanol
SCE: Super Critical Fluid Extraction

BRIEF DESCRIPTION OF THE DRAWINGS

The features, aspects and advantages of the present invention will become better understood when the following detailed description is read with reference to the accompanying drawings in which like characters represent like parts, wherein.

DETAILED DESCRIPTION OF THE INVENTION

The present invention relates to a process for the isolation and purification of cannabinoids from *Cannabis* plant material of different varieties. The present process comprises the following steps:

a) extracting the plant material using optionally an organic solvent of supercritical fluid with or without modifier followed by evaporation of the extraction solvent to yield a crude extract;

b) optionally winterizing the crude extract prior to derivatization to remove hydrocarbons and waxes and derivatizing the crude extract, or optionally thin film distilled extract with a t-boc-amino acid to convert cannabinoids to their t-boc-amino acid esters;

c) purifying the derivatized extract using normal phase column chromatography to isolate individual esters of different cannabinoids;

d) base hydrolyzing the isolated individual cannabinoid ester to regenerate the free cannabinoid with high purity (>90% pure-100% pure); and e) optionally re-chromatographing the isolated cannabinoids to increase purity to a desired level.

The process extraction solvent in the present process is a hydrocarbon such as, for example, n-pentane, hexanes or heptane. The extraction is carried out using supercritical fluid using $CO_2$ with or without a modifier such as acetone, ethanol or methanol.

The crude extract is subjected to a thin film distillation step under reduced pressure to increase the cannabinoid content of the extract.

The t-boc-amino acid is selected from but not limited to tryptophan, glutamine, alanine and phenylalanine.

The cannabinoid of interest in the present process can be $\Delta^9$-tetrahydrocannabinol ($\Delta^9$-THC or THC), cannabidiol (CBD), $\Delta^9$-tetrahydrocannabivarin (THCV) or cannabigerol (CBG).

Example No. 1

Production of CBD from the Decarboxylated Extract of a High CBD Variety of *Cannabis*

Extraction and Decarboxylation:

Air-dried and powdered buds (274 g) of a high CBD variety of *Cannabis* (3.0% CBD) were extracted by maceration at room temperature with hexanes (Fisher, H-302-4) for 24 hours (1.0 L hexanes×3). The hexanes extracts were combined and evaporated under vacuum to give 19.5 g of extract which was decarboxylated by heating at 130° C. for 30 minutes to give 16.6 g of decarboxylated extract (40% CBD by GC/FID analysis).

Chemical Derivatization:

A portion (7.8 g) of the decarboxylated extract was dissolved in 100 mL methylene chloride (DCM, Fisher, D37-4) to which dimethylaminopyridine (DMAP) (65 mg) was added, and the reaction mixture stirred at room temperature for 10 minutes, (mixture A). In another 1 L round bottom flask, Boc-Trp-OH (15.8 g, 2.1 eq, AnaSpec Inc, 510-791-9560) was mixed with DCC (10.7 g, 2.1 eq., Alfa Aesar, A13016) and DCM (100 mL), the reaction mixture was stirred at room temperature for 10 minutes, (mixture B). Mixture B was then added to mixture A, followed by stirring at room temperature for 15 minutes for the reaction completion, which was confirmed by Si gel Thin Layer Chromatography (Si-TLC) using ethyl acetate (EtOAc, Fisher, E145-4): DCM (5:95) as the mobile phase. After the reaction was complete, 400 mL of hexanes was added and the mixture was cooled in the freezer for 4 hours followed by filtration through a filter funnel. The filtrate was evaporated to dryness under reduced pressure to give 29.0 g of the dried reaction mixture.

Column Chromatography:

The reaction mixture (29 g), dissolved in 20 mL of DCM, was applied to the top of a silica gel (750 g, Silicycle 60 A, R 100303) column (dimensions: 5×80 cm). Elution was carried out using 2% EtOAc/DCM, and four fractions (A-D) were collected. Fraction B (9.3 g), which was rich in the CBD adduct was evaporated and the residue was used in the next step.

Hydrolysis of CBD Adduct Fraction (Fraction B):

The CBD adduct fraction (9.3 g) was dissolved in 3 mL methanol (MeOH, Fisher, A452-4), then 10 mL KOH (5N) was added and the mixture stirred at room temperature for a few minutes to allow complete hydrolysis which was checked by TLC. After completion of hydrolysis, HCl (5N) was added to neutralize the excess base and release the free CBD, followed by extraction with DCM. The organic layer was separated and dried in vacuo and then 100 mL hexanes was added to precipitate any excess reagents which are removed by filtration. The filtrate was evaporated to dryness under reduced pressure to yield 3.0 g of crude CBD (89.9% by GC/FID analysis).

Column Chromatography of the Impure CBD:

The impure CBD fraction (3.0 g) was dissolved in 5 mL DCM then applied to a Si gel column eluted with an isocratic mixture of EtOAc:hexanes (2.5:97.5) to give four fractions. The results are summarized in Table 1.

TABLE 1

| CBD Fractions by Process of Example 1 | | |
|---|---|---|
| Fraction | Weight (g) | Analysis for CBD |
| 1-2 | 0.075 | — |
| 3 | 1.875 | 100% |
| 4-9 | 0.634 | 98.8% |
| 10-11 | 0.552 | 1.8% |

Figure 1:
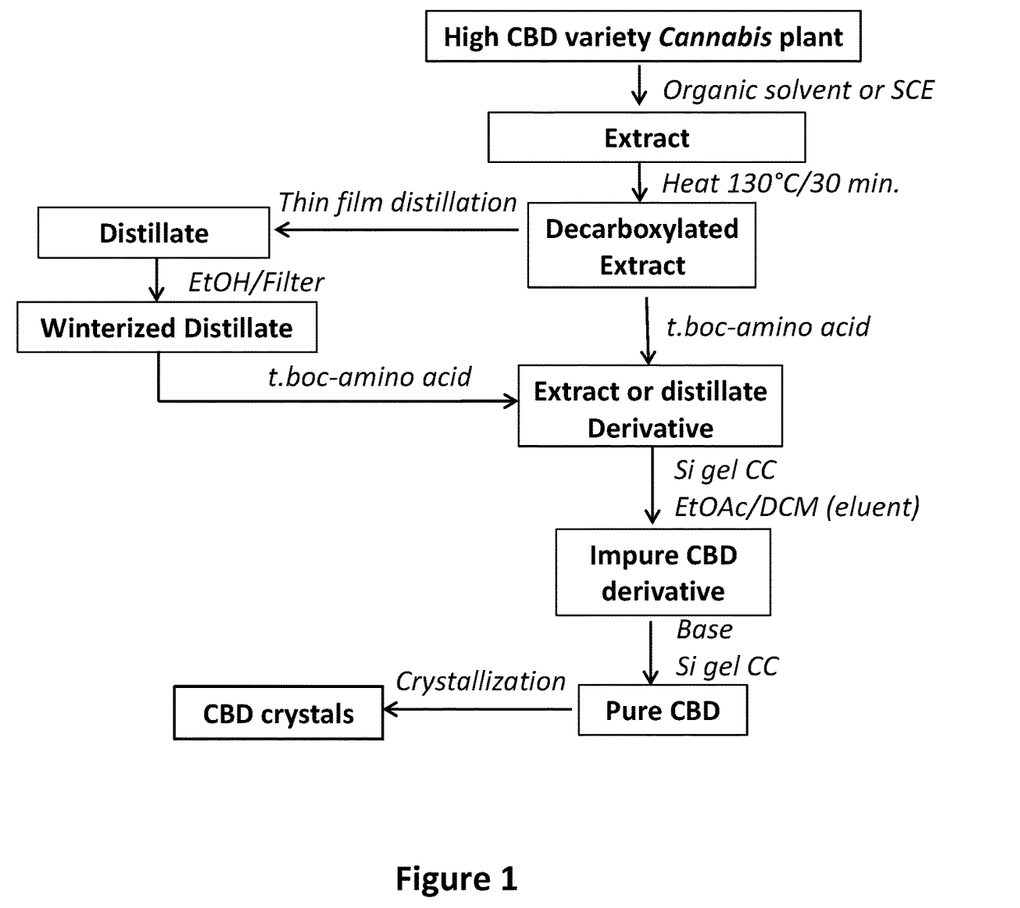
FIG. 1 is a schematic representation to produce CBD.

Fractions 3 and 4-9 were combined and crystallized from hexanes to give 2.2 g of CBD as pale yellow cubic crystals with 100% purity. The purity of CBD was confirmed by GC/FID, GC/MS and NMR spectroscopic analysis. The overall yield of this process starting from decarboxylated extract to the pure CBD was 70.5%. FIG. 1 shows the schematic representation of this process.

Example No. 2

Production of CBD from the Decarboxylated and Winterized Distillate of an Extract of CBD Rich Variety of *Cannabis*

Plant Material Extraction:

Dried and powdered *Cannabis* plant material (3.00 Kg) of CBD rich variety of *Cannabis* (4.03% CBD) was extracted by maceration in hexanes (20 L×2) followed by evaporation under reduced pressure to give 182.3 g dried extract (52.2% CBD).

Thin Film Distillation of the Crude Extract:

The hexane extract (182.3 g) was decarboxylated by heating in an oil bath for 30 minutes at 130° C., to give 162 g of decarboxylated extract. The process was monitored by TLC analysis and GC/FID of the TMS derivative or by HPLC to confirm complete decarboxylation. The decarboxylation step is essential to prevent frothing of the extract during the distillation process. The decarboxylated extract (153.0 g) was subjected to distillation using thin film distillation with the following conditions:

Vacuum: 44 m Torr
Temperature: 199° C.
Rotation: 300 rpm
Flow rate: 2 mL/min.

The produced distillate (98.0 g) has golden yellow color and its CBD content is 67.7% (Recovery of CBD in this step is 70.0%). Volatile substances (7.88 g, 11.2% CBD) and residue (37.10 g, 25.5% CBD) were also collected after the distillation was completed.

Winterization of the Distillate:

Crude *Cannabis* extract as well as the thin film distillate are known to contain high concentration of waxes and hydrocarbons. These could be substantially removed or reduced by the following process, referred to as "Winterization Process".

The distillate (98.0 g) was dissolved in 200-proof ethanol at a ratio of 1 part extract to 12 parts ethanol (1.17 L). The ethanol solution of the distillate was then placed in the freezer (−20° C.) for 4 hours. While cold, the precipitated material was filtered out using a filter funnel and the filter was rinsed with 100 mL of ice cold ethanol. The filtered ethanolic solution of the distillate was evaporated to dryness to give 84.0 g residue (78% CBD content). The CBD recovery in this step is 99.0%.

Chemical Derivatization:

A portion of the above residue (14.0 g, 78% CBD) was dissolved in 50 mL DCM and to which 120 mg of DMAP was added, and the reaction mixture was stirred for 10 minutes (mixture A). In another 1 L round bottom flask, Boc-Trp-OH (28.4 g, 2.1 eq.) was mixed with DCC (19.2 g, 2.1 eq.) in 200 mL DCM and the reaction mixture was stirred at room temperature for 10 minutes (mixture B). Mixture B was added to mixture A then the reaction mixture was stirred till the reaction was complete (approximately 15 minutes) which was confirmed by Si gel Thin Layer Chromatography (Si-TLC) using Ethyl acetate (EtOAc, Fisher, E145-4):DCM (5:95) as the mobile phase. After completion of the reaction, 700 mL hexanes was added to the reaction product and kept in the freezer for 4 hours then filtered. The filtrate was evaporated to dryness under reduced pressure to give 46.5 g dried distillate adduct.

Column Chromatography:

A portion of the crude distillate adduct (22.4 g) was dissolved in 50 mL DCM and applied on the top of a Si gel column (750 g) and the material eluted with 2% EtOAc/DCM. Seventeen fractions were collected and similar fractions are combined based on TLC analysis. The results are shown in Table 2.

TABLE 2

CBD Fractions by Process of Example 2

| Fraction | Weight (g) | Analysis for cannabinoids |
|---|---|---|
| 1-7 | 2.67 | — |
| 8 | 1.90 | CBD adduct of 23% CBD contents |

TABLE 2-continued

CBD Fractions by Process of Example 2

| Fraction | Weight (g) | Analysis for cannabinoids |
|---|---|---|
| 9-17 | 14.4 | CBD adduct rich fraction of 27% CBD content |

The CBD adduct Fraction (14.4 g) was subjected to alkaline hydrolysis as above to give 4.7 g of CBD (82% CBD contents).

Column Chromatography of the Crude CBD:

The crude CBD fraction (4.7 g) was dissolved in 5 mL DCM then applied to a Si gel column eluted with 2.5% EtOAc/hexanes to yield three fractions. The results are summarized in Table 3.

TABLE 3

Crude CBD Fractions by Process in Example 2

| Fraction | Weight (g) | Analysis for CBD |
|---|---|---|
| 1-6 | 2.85 | 99.98% |
| 7-11 | 0.358 | 98.2% |
| 12-16 | 1.266 | — |

Fractions 1-6 and 7-11 were combined and crystallized from hexanes to give 3.18 g of CBD as pale yellow cubic crystals with 100% purity. The overall yield of CBD in this process starting from the decarboxylated extract to the pure CBD was 61%.

The schematic representation of this process is shown in FIG. 1.

Example No. 3

Production of CBD from an Extract of an Intermediate Variety of *Cannabis* Containing High CBD and High THC Plant Material Extraction:

Air dried powdered *Cannabis* plant (0.81 Kg) of Intermediate variety CBD variety (6.3% CBD and 2.96% THC) was extracted by maceration in hexanes (5.0 L×2) followed by evaporation under reduced pressure to yield 126.0 g dry extract (42.8%. CBD, 20.4% THC). Portion of the extract (27.14 g) was decarboxylated by heating in an oil bath at 130° C. for 30.0 min. to give 23.6 g of the decarboxylated extract (45.7% CBD, 19.4% THC).

Chemical Derivatization and Purification of the CBD and THC Adducts:

The decarboxylated extract (23.6 g) was chemically derivatized as before, using t-Boc-Trp-OH, to produce adduct. 1.2 L hexanes was added to the reaction product and kept in the freezer for 4 hours then filtered. The filtrate was evaporated to dryness under reduced pressure to give 79.75 g dried distillate adduct. Portion of the adduct (26.43 g) was purified by Si gel column chromatography (800 g Si) eluted with 2% EtOAc/DCM. Five fractions were collected, and details are shown in the next Table.

TABLE 4

CBD Fractions by Process of Example 3

| Fraction | Weight (g) | Analysis for Cannabinoids |
|---|---|---|
| 1-6 | 1.2 | — |
| 7-15 | 3.73 | 43% THC contents |
| 16-17 | 0.84 | — |
| 18-19 | 9.3 | 32% CBD content |
| 20-22 | 10.0 | |

Purification of CBD:

The CBD rich column fraction (9.3 g) was hydrolyzed by dissolving in 3 mL MeOH, then 10 mL KOH (5N) were added and stirred at room temperature for 5 min. to allow complete hydrolysis which was checked by TLC. HCl 6N was added till neutralization followed by extraction with DCM. The organic layer was separated and dried in vacuo and then 100 mL hexanes were added to precipitate any excess reagents followed by filtration. The filtrate was evaporated till dryness under reduced pressure to yield CBD (90%), 3.0 g of that was purified by Si gel column chromatography using EtOAc/hexanes (2.5%) as an eluent, 50 mL fractions were collected. The result was shown in Table 5.

TABLE 5

CBD Fractions by Process of Example 3

| Fraction | Weight (g) | Analysis for Cannabinoids |
|---|---|---|
| 1-3 | 0.046 | — |
| 4-6 | 1.89 | CBD 100% |
| 7-10 | 0.146 | CBD 97% |
| 11-15 | 0.108 | CBD 84%, CBG 8.3% |
| 16-17 | 0.11 | CBD 0.3%, CBG 98.9% |
| 18-19 | 0.09 | — |

The CBD from fractions 4-6 was crystallized from hexanes to yield 1.89 g CBD as pale yellow crystals (100% pure), with over all yield of 54% starting from the decarboxylated extract.

Figure 2:
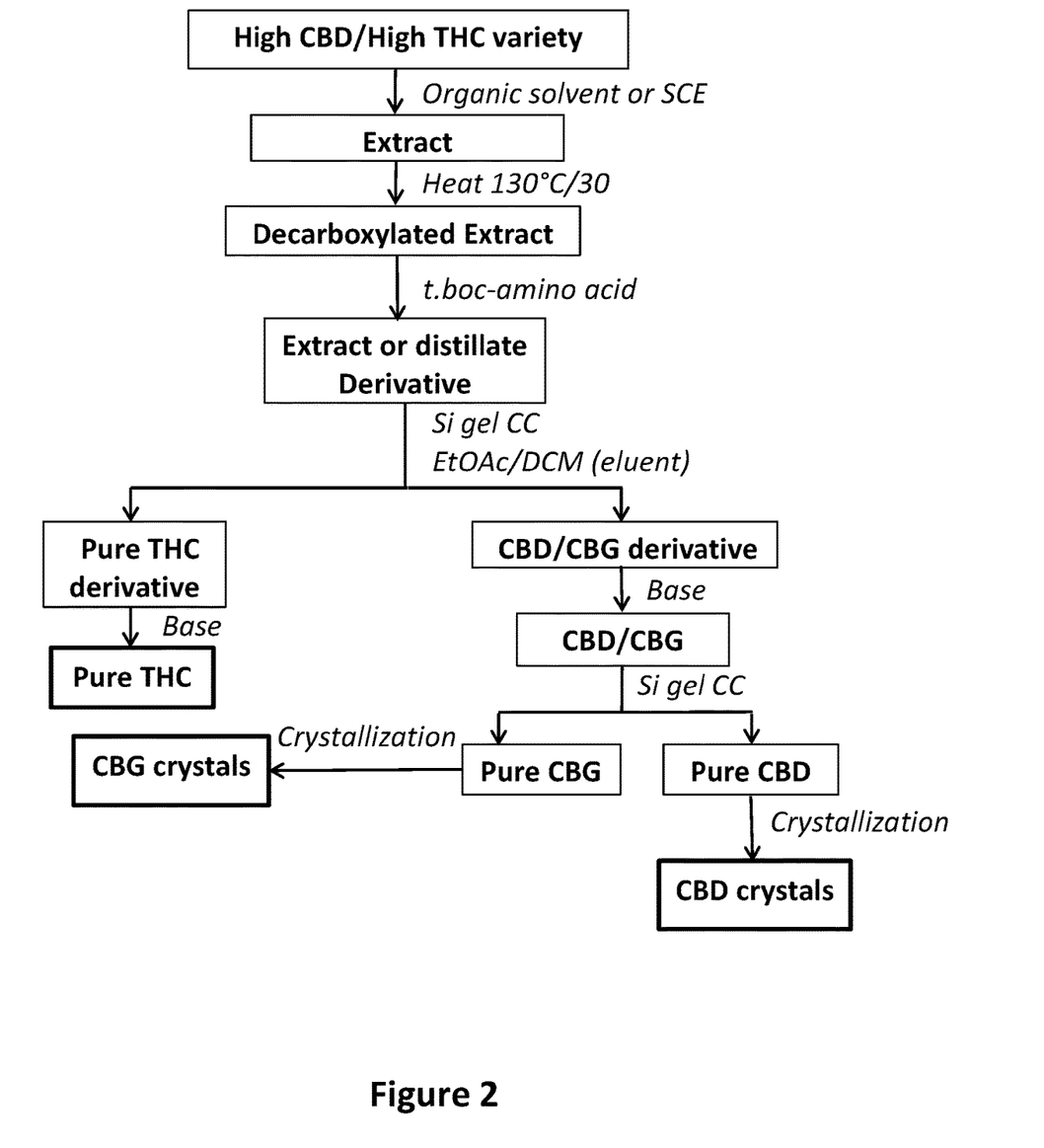
FIG. 2 is a schematic representation to produce THC, CBD and CBG.

Purification of THC:

The THC rich column fraction 7-15 (3.73 g) was chromatographed over Si gel column eluted with 2% EtOAc/DCM (50 mL/fraction) to give 2.2 g pure THC adduct which was hydrolyzed using KOH (5N) to yield 0.96 g THC (97.49% purity) with an overall yield of 60% starting from the decarboxylated extract. The impurities in the THC are basically due to CBN (2.51%), which is a known oxidation product of THC normally found in pharmaceutical grade THC. The schematic representation of the production of THC and CBD was shown in FIG. 2.

Example No. 4

Production of THC from the Distillate of an Extract of High Potency Variety of Cannabis (High THC)
Plant Material Extraction:

Air-dried and powdered high potency Cannabis plant material (17.20 Kg) of high THC content (>8%) was extracted at room temperature by overnight maceration and percolation with hexanes (80 L×2), followed by evaporation under reduced pressure at 60° C. to give 2.32 kg dry extract (66.4% THC).

Thin Film Distillation of the Crude Extract:

High potency extract (630 g) was heated at 130° C. for 30 min then subjected to distillation using thin film distillation still under the following conditions:

Vacuum: 120 m Torr
Temperature: 199° C.
Rotation: 300 rpm
Flow rate: 2 mL/min.

After completion of the distillation process, the distillate (465 g; 73.8% yield) was obtained along with volatile oil fraction (57 g) and undistilled residue (70 g). The THC content of the distillate was 71.5%.

Chemical Derivatization of the Distilled Extract:

A portion (103.9 g) of the distillate was winterized by ethanol to remove waxes and hydrocarbons to produce 85.0 g (77% THC) winterized distillate, of which 39.5 g was chemically derivatized as following:

The distillate (39.5 g) was dissolved in 100 mL methylene chloride (DCM, Fisher, D37-4) to which was added DMAP (120 mg) and the reaction mixture was stirred at room temperature for 10 minutes (mixture A). In another 2 L round bottom flask, Boc-Trp-OH (45.0 g, 1.2 eq, AnaSpec. Inc, 510-791-9560) was mixed with DCC (31.1 g, 1.2 eq., Alfa Aesar, A13016) then 100 mL DCM were added and the reaction mixture was stirred at room temperature for 10 minutes (mixture B). Mixture B was added to mixture A and the reaction mixture was stirred at room temperature until the reaction was completed (approx. 15 mins.), which was confirmed by Si gel Thin Layer Chromatography (Si-TLC) using EtOAc:DCM (5:95) as mobile phase. After the reaction completion, 2 L hexanes was added and the precipitated reagents were filtered. The filtrate was evaporated to dryness under reduced pressure to give 116.0 g dried distillate adduct.

Column Chromatography:

The reaction mixture (116.0 g) was dissolved in 100 mL of DCM and loaded on the top of a silica gel column (2.3 Kg, Silicycle 60 A, R 100303). Isocratic elution was performed using 2% EtOAc/DCM. Three fractions (A-C) were collected as summarized in Table 6.

TABLE 6

THC and CBD fractions by the process described in Example 4

| Fraction | Weight (g) | Analysis for Cannabinoids |
|---|---|---|
| A | 25.0 | Complex mixture and reagents |
| B | 20.0 | THC adduct and CBN adduct |
| C | 50.0 | THC adduct |

Hydrolysis of THC Adduct:

Fraction C (50.0 g) was subjected to hydrolysis using 5N KOH to give 23 g THC with 98.90% purity. The purity of THC was determined by GC/FID and GC/MS analysis. The overall yield of THC from this process starting from the distilled extract is 75%. The schematic representation of this process was shown in FIG. 3.

Example No. 5

Production of THC from the Distillate of an Extract of a High THC Variety of Cannabis
Extraction and Decarboxylation:

Dried plant material (31.126 kg) of high THC content Cannabis (9.96%) was extracted by hexanes (140 L) in 200 L percolator, for 12 hours, then the extract was drained and evaporated under reduced pressure at 60° C. till dryness. The dried extract was heated at 100° C. for 5 hours till complete decarboxylation which was detected by TLC to give 4.16 Kg extract (THC content 52.9%).

Distillation of the Decarboxylated Extract:

A portion of the above extract (1.38 kg) was distilled using thin film distillation as above to give 870 g distillate. The distillate was dissolved in 10 L EtOH and kept in the freezer for 4 hours, then filtered to remove waxes and hydrocarbons. The filtrate was concentrated under reduced pressure to yield 667 g of winterized extract.

Chemical Derivatization:

A portion of the distillate (50.0 g) was chemically derivatized by reaction with t-Boc-try-OH and DCC as above to produce distillate adduct. 2.5 L hexanes was added and the precipitated reagents were filtered. The filtrate was evaporated to dryness under reduced pressure to give 110 g dried distillate adduct.

Purification of the Distillate Adduct to Produce THC Adduct:

The adduct was dissolved in DCM and applied on a silica gel column (2.0 Kg), eluted with 2% EtOAc/DCM, to produce 4 fractions A-D in Table 7.

TABLE 7

THC and CBD fractions by the process described in Example 5

| Fraction | Weight (g) | Analysis for Cannabinoids |
|---|---|---|
| A | 7.9 | Complex mixture and reagents |
| B | 13.0 | THC/CBN adduct, |
| C | 37.0 | THC adduct |
| D | 30.1 | — |

Figure 3:
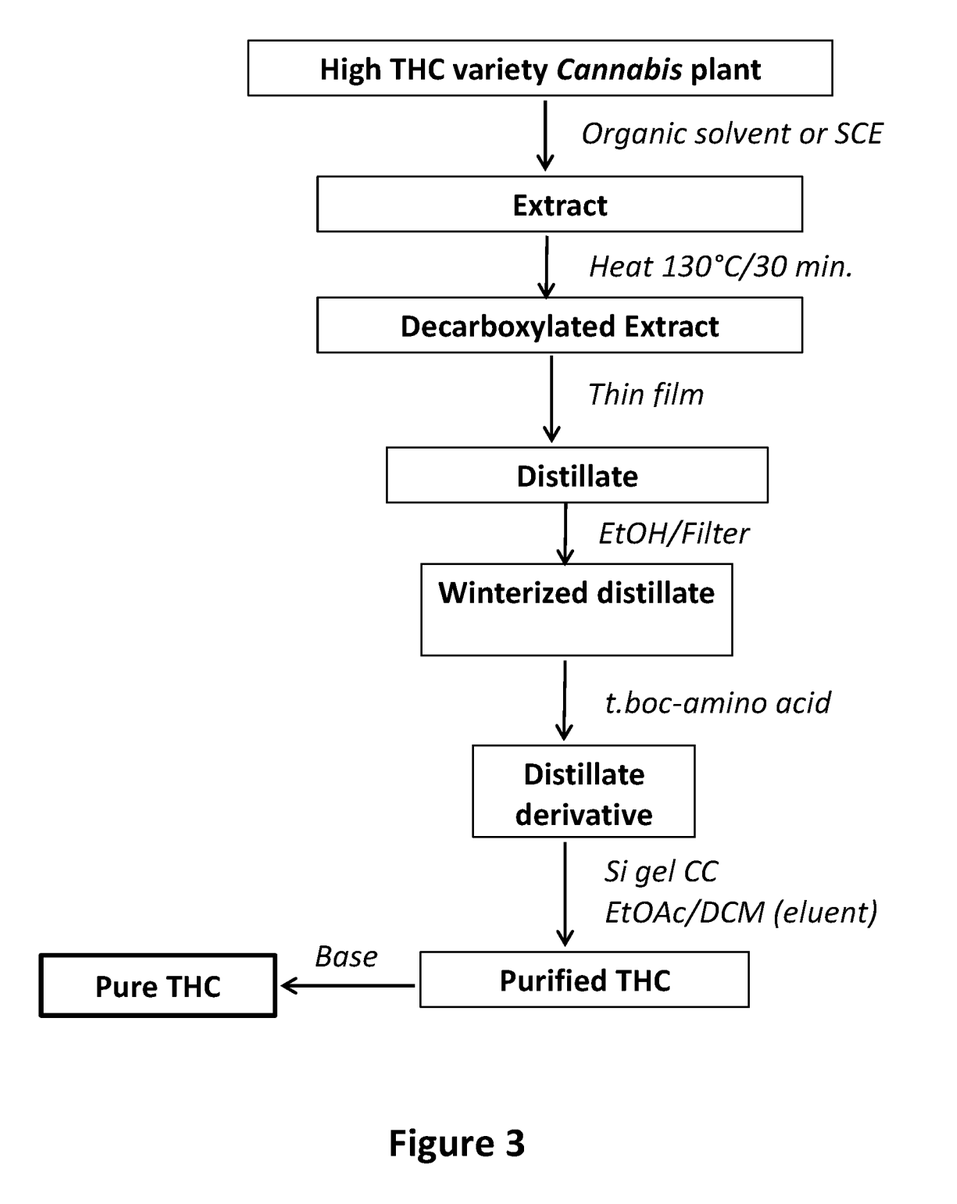
FIG. 3 is a schematic representation to produce THC.

Hydrolysis of THC adduct (37.0 g) was performed using 5N KOH to produce 15.9 g THC of 98.2% purity. The overall yield of THC in the process starting from the decarboxylated extract is 60.2%. FIG. 3 shows the schematic representation of this process.

Example No. 6

Purification of $\Delta^9$-THCV from a High THCV Cannabis Fraction

Preparation of Reaction Material:

A fraction rich in $\Delta^9$-THCV (69.0% THCV, 1.70 g) was dissolved in 50 mL methylene chloride (DCM, Fisher, D37-4) to which 4-Dimethyl aminopyridine (10.0 mg) was added, and reaction mixture stirred at room temperature for 10 minutes, (mixture A). In another 500 mL round bottom flask, Boc-Gln-OH (1.62 g, 1.2 eq, Aldrich, 408441) was mixed with DCC (1.5 g, 1.2 eq., Alfa Aesar, A13016) and DCM (50 mL), and the reaction mixture was stirred at room temperature for 10 minutes, (mixture B). Mixture B was then added to mixture A, followed by stirring at room temperature for 15 minutes for the reaction completion, which was confirmed by Si gel Thin Layer Chromatography (Si-TLC) using ethyl acetate (EtOAc, Fisher, E145-4):DCM (5:95) as the mobile phase. After the reaction was complete, 100 mL hexanes was added and the mixture was cooled in the freezer for 4 hours, followed by filtration through a filter funnel. The filtrate was evaporated to dryness under reduced pressure to give 4.3 g of the dried reaction mixture.

Figure 4:
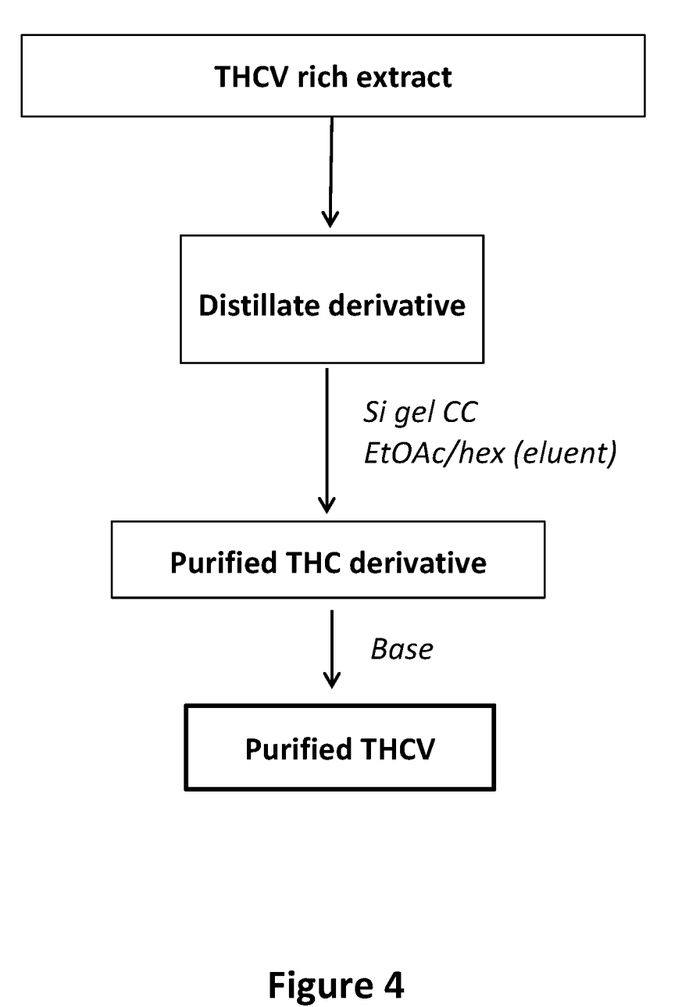
FIG. 4 is a schematic representation to produce THCV.

Column Chromatography:

The reaction mixture (4.3 g) dissolved in 5 mL of DCM was applied to the top of a silica gel column (65.0 g, Silicycle 60 A, R 100303). Elution was carried out using 5% EtOAc/hexanes, and four fractions (A-D) were collected. Fraction C (917 mg), which contains pure THCV adduct, was hydrolyzed using 5N KOH to give 419 mg $\Delta^9$-THCV with 95.0% purity. The purity was determined using GC/FID and GC/MS. The overall yield of $\Delta^9$-THCV is 35%. FIG. 4 shows the schematic representation of this process.

Example No. 7

Purification of CBG:

The column fraction 16-17 (0.11 g, 98.9% purity) from experiment No. 3 was subjected to crystallization from hexanes to give 0.10 g CBG as white needles with 100.0% purity as determined by GC/FID and GC/MS. The schematic representation of this process was shown in FIG. 2.

Preparation of CBD from a High CBD Cannabis Extract

In the case of a Cannabis extract that has a high CBD content and a low THC content, purification of CBD can be carried out much more efficiently without prior derivatization.

The crude extract (hexanes extract or supercritical fluid extract) could be winterized and the winterized extract subjected to a process of thin film distillation and the distillate chromatographed directly without derivatization.

Below are examples of the processes.

Example No. 8

Production of CBD from a High CBD Distillate

Three batches, 5.0 g each of High CBD Winterized distillate (78% CBD and 10% THC) were subjected to Si gel CC (100 g silica each) eluted with 2.5% EtOAc/hexanes. Four fractions 200 mL each were collected and analyzed by TLC using DCM as an eluent. Fractions 2 and 3 were combined and concentrated under vacuum, then dissolved in 20 mL hexanes, and then kept in the freezer for 15 hrs. The supernatant was decanted and the crystals were washed with cold hexanes (5 mL). The yield and the GC analysis are shown in Table 8.

TABLE 8

CBD Produced by Process in Example 8

| Batch # | Wt. (g) | CBD Recovery | CBD purity | THC % | Other cannabinoids % |
|---|---|---|---|---|---|
| B# 1-CBD | 3.2 g | 81.4% | 99.2% | 0.22 | 0.15% THCV 0.36% other peak |
| B# 2-CBD | 2.4 | 61.53% | 99.3% | 0.28 | 0.08% THCV 0.30% other peak |
| B# 3-CBD | 2.86 | 72.77% | 99.2% | 0.35 | 0.08% THCV 0.29% other peak |
| Average CBD and THC in the crystals | 2.83 g | 71.9% | 99.23% | 0.28% | 0.3% other peak 0.1% THCV |

Example No. 9

Production of CBD Crystals from a High CBD Distillate

Two high CBD extracts (300 g) were distilled by thin film distillation, then winterized with ethanol to give two winterized distillates (215 g and 205 g). Each winterized distillate was subjected to Si gel CC followed by crystallization to yield three batches of pure CBD (>99.9% purity) as follow:

a—Winterized distillate Batch #1 (215 g, 75.05% CBD and 2.2% THC) was subjected to silica gel cc chromatography (3.0 kg silica) isocratically eluted with 2.5% EtOAc/ hexanes. Eleven fractions (2 L each) were collected and examined by TLC (DCM as eluent), then similar fractions were combined to give three main fractions (A-C). Fraction B that showed single spot was crystallized from hexanes at room temperature to give 106.05 g of pure CBD (99.93% purity).

b—Winterized distillate Batch #2 (205 g, 75.7% CBD and 2.2% THC) was also subjected to silica gel cc chromatography (3.0 kg silica) then crystallization as described for batch #1 to produce 108.2 g of crystalline CBD with purity=99.95%.

Table 9 shows the yield and the purity (by GC analysis) of two batches of CBD.

TABLE 9

CBD Produced by Process in Examole 9

| Batch # | Wt. (g) | CBD Recovery | CBD purity | THC % | Other cannabinoids % |
|---|---|---|---|---|---|
| B# 1-CBD | 215 g | 65.75% | 99.93% | <0.01 | 0.07% |
| B# 2-CBD | 205 g | 68.5% | 99.95% | <0.01 | 0.05% |
| Average CBD and THC in the crystals | 2.10 g | 67.1% | 99.94% | <0.01 | 0.06% |

REFERENCES

1. ElSohly, M. A.; Harland, E.; and Waller, C. W.; Cannabinoids in glaucoma II: The effect of different cannabinoids on the intraocular pressure of the rabbit; Curr. Eye Res., 3(6): 841-850, 1984.
2. El-Mallakh, R. S.; Marihuana and migraine, Headache, 27(3):442-443, 1987.
3. Volfe, Z.; Dvilansky, I. A.; and Nathan, I.; cannabinoids in block release of serotonin from platelets induced by plasma from migraine patients; Int. J. Clin. Pharmacol. Res., 5(4):243-246, 1985.
4. Maurer, M.; Henn, V.; Dirtrich, A.; and Hofmann, A.; Delta-9-tetrahydrocannabinol shows antispastic and analgesic effects in single case double-blind trial; Eur. Arch. Psychiatry Clin. Neurosci., 240(1): 1-4, 1990.
5. McLendon, D. M.; Harris, R. T.; and Maule, W. F.; Suppression of the cardiac conditioned response by delta-9-tetrahydrocannabinol: A comparison with other drugs; Psychopharmacology, 50(2): 159-163, 1976.
6. ElSohly, Mahmoud A.; Stanford, Donald F.; Harland, Ernest C.; Hikal, Ahmed H.; Walker, Larry A.; Little, Thomas L., Jr.; Rider, James N.; and Jones, Alan B.; Rectal bioavailability of delta-9-tetrahydrocannabinol from the hemisuccinate ester in monkeys; J. Pharm. Sci., 80(10): 942-945, 1991.
7. ElSohly, Mahmoud A.; Little, Thomas L., Jr. Hikal, Ahmed; Harland, Ernest; Stanford, Donald F. and Walker, Larry; Rectal bioavailability of delta-9-tetrahydrocannabinol from various esters; Pharmacol., Biochem., Behav., 40(3): 497-502, 1991.
8. Mattes, Richard D.; Shaw, Leslie M.; Edling-Owens, Judy; Engelman, Karl; and ElSohly, Mahmoud A.; Bypassing the first-pass effect for the therapeutic use of cannabinoids: Pharmacol., Biochem., Behav., 44(3): 745-77, 1993.
9. Mather L.; Cannabinoid pharmacotherapy: past, present and future: Minerva Anestesiologica, 71(7-8):405-12, 2005.
10. Brenneisen, R.; ElSohly, M. A.; Henn, V.; and Spiess, Y.; The effect of orally and rectally administered delta-9-tetrahydrocannabioi on spasticity: A pilot study with 2 patients; Inter. J. Clin. Pharmacol. and Therapeutics, 34(10): 446-452, 1996.
11. Cunha, Jomar M., E. A. Carlini, Aparecido E. Pereira, Oswaldo L. Ramos, Camila Pimentel, Rubens Gagliardi, W. L. Sanvito, N. Lander, and R. Mechoulam. "Chronic administration of cannabidiol to healthy volunteers and epileptic patients." Pharmacology 21: 175-185, 1980.
12. Mechoulam, Raphael, Linda A. Parker, and Ruth Gallily. "Cannabidiol: an overview of some pharmacological aspects." The Journal of Clinical Pharmacology 42, no. S1: 11S-19S, 2002.
13. Schier, Alexandre Rafael de Mello, Natalia Pinho de Oliveira Ribeiro, Jaime Eduardo Cecilio Hallak, Jose Alexandre S. Crippa, Antonio E. Nardi, and Antonio Waldo Zuardi. "Cannabidiol, a *Cannabis sativa* constituent, as an anxiolytic drug." Revista Brasileira de Psiquiatria 34 (: 104-110, 2012.
14. Brenda E. Porter, Catherine Jacobson Report of a parent survey of cannabidiol-enriched *cannabis* use in pediatric treatment-resistant epilepsy). Epilepsy & Behavior, 29, 5745-577, 2013.
15. Lola Weissd, Michael Zeira, Raphael Mechoulam, Shimon Salvin, Ruth Gallity. Treating or preventing diabetes with Cannabidiol. U.S. Pat. No. 8,071,641 B2, issued Dec. 6, 2011.
16. Lannotti, Fabio Arturo; Hill, Charlotte L.; Leo, Antonio; Alhusaini, Ahlam; Soubrane, Camille; Mazzarella, Enrico; Russo, Emilio; Whalley, Benjamin J.; Di Marzo, Vincenzo; Stephens, Gary J. Nonpsychotropic Plant Cannabinoids, Cannabidivarin (CBDV) and Cannabidiol (CBD), Activate and Desensitize Transient Receptor Potential Vanilloid 1(TRPV1) Channels in Vitro: Potential for the Treatment of Neuronal Hyperexcitability ACS Chemical Neuroscience, 5(11): 1131-1141, 2014.
17. Prakash S. Nagarkatti, Mitzi Nagarkatti, Use of cannbaindiol in the treatment of autoimmune hepatitis US patent Aug. 14, 2012.
18. Geoffrey Guy, Bettina Platt, (2014). Cannabinoid-containing plant extracts as neuroprotective agents, U.S. Pat. No. 8,673,368.
19. Gaoni Y, Mechoulam R. Isolation, structure, and partial synthesis of an active constituent of hashish. J. Am. Chem. Soc. 86(8): 1646-1647, 1964.
20. ElSohly, Mahmoud A.; and Ross, Samir A.; Method of preparing delta-9-tetrahydrocannabinol; U.S. Pat. No. 6,365,416, B1: Apr. 2, 2002.
21. Duchek, John Robert; Cannabinoid crystalline derivatives and process of cannabinoid purification; U.S. Pat. No. 7,402,686 B2: Jul. 22, 2008.
22. Adams, R.; Hunt, M.; Clark, J. H.; Structure of cannabidiol, a product isolated from the marihuana extract of Minnesota wild hemp; J. Amer. Chem. Soc. (62): 196-200, 1940.
23. Adams, R.; Pease, D. C.; Clark, J. H.; Isolation of cannabinol, cannabidiol from red oil of Minnesota wild hemp; J. Amer. Chem. Soc. (62): 2194-2196, 1940.
24. Hazekamp, A.; Simon, R.; Looman, A. P.; Sengers, M.; Zweden, R. V.; and Verpoorte, R.; Preparative isolation of cannabinoids from *Cannabis sativa* by centrifugal Partition Chromatography; J. Liquid Chroma. and Related Tech., 27: 2421-2439, 2004.
25. Appendio, G.; Gibbons, S.; Giana, A.; Pagani, A.; Starvi, M.; Smith, E.; and Mukhlesur, R., Antibacterial cannabinoids from *Cannabis sativa*: A structure-activity study; J. Nat. Prod., 71: 1427-1430, 2008.

26. Flockhart Ian, Ehjeatley Gray, Dring Su, Lesley Archer. Method of preparing Cannabidiol from plant material; U.S. Pat. No. 0,167,283: Jul. 27, 2006.

What is claimed is:

1. A process for the isolation and purification of cannabinoids from *Cannabis* plant material of different varieties comprising the following steps:
    a) extracting the plant material using an organic extraction solvent of supercritical fluid with or without modifier followed by evaporation of the extraction solvent to yield crude extract;
    b) optionally winterizing the crude extract prior to derivatization to remove hydrocarbons and waxes and derivatizing the crude extract, or optionally thin film distilled extract with a t-boc-amino acid to convert cannabinoids to their t-boc-amino acid esters;
    c) purifying the derivatized extract using normal phase column chromatography to isolate individual esters of different cannabinoids;
    d) base hydrolyzing the isolated individual cannabinoid ester to regenerate the free cannabinoid with high purity greater than 90% pure; and
    e) optionally re-chromatographing the isolated cannabinoids to increase purity to a desired level.

2. The process of claim 1, where the extraction solvent is a hydrocarbon.

3. The process of claim 1, where extraction is carried out using supercritical fluid using $CO_2$ with or without a modifier.

4. The process of claim 1, where the crude extract is subjected to a thin film distillation step under reduced pressure to increase the cannabinoids content of the extract.

5. The process of claim 1, where the crude extract is winterized to remove hydrocarbons and waxes.

6. The process of claim 4, where the thin film distilled extract is winterized to remove hydrocarbons and waxes.

7. The process of claim 1, where the t-boc-amino acid is selected from tryptophan, glutamine, alanine, or phenylalanine.

8. The process of claim 1, where a cannabinoid of interest is $\Delta^9$-tetrahydrocannabinol.

9. The process of claim 1, where a cannabinoid of interest is cannabidiol.

10. The process of claim 1, where a cannabinoid of interest is $\Delta^9$-tetrahydrocannabivarin.

11. The process of claim 1, where a cannabinoid of interest is cannabigerol.

12. The process of claim 2, wherein the hydrocarbon is an n-pentane, hexane or heptane.

13. The process of claim 3, wherein the modifier is acetone, ethanol or methanol.

* * * * *